United States Patent [19]
Peifer

[11] Patent Number: 5,699,575
[45] Date of Patent: Dec. 23, 1997

[54] FLEXIBLE ROTARY TOOTHBRUSH

[76] Inventor: Melvin W. Peifer, R.R. 2, Box 349-H, Millville, Pa. 17846

[21] Appl. No.: 546,679

[22] Filed: Oct. 23, 1995

[51] Int. Cl.⁶ .................... A61C 17/26; A61L 2/10
[52] U.S. Cl. .................... 15/23; 15/257.01; 312/229; 312/223.1; 422/24; 422/300
[58] Field of Search .................... 15/1, 22.1, 23, 15/38, 257.01; 312/209, 223.1; 422/24, 300

[56] References Cited

U.S. PATENT DOCUMENTS

| | | | |
|---|---|---|---|
| 1,593,763 | 7/1926 | Henderson | 15/23 |
| 2,235,296 | 3/1941 | Muncheryan | 15/257.01 |
| 2,314,117 | 3/1943 | Beckner | 15/23 |
| 2,840,837 | 1/1958 | Gustems . | |
| 3,451,086 | 6/1969 | Burgett . | |
| 3,739,416 | 6/1973 | Kurachi . | |
| 3,776,694 | 12/1973 | Leittl | 312/209 |
| 3,822,432 | 7/1974 | Skinner . | |
| 3,829,922 | 8/1974 | Koblanski . | |
| 4,275,749 | 6/1981 | Caroli . | |
| 4,344,202 | 8/1982 | Hayat . | |
| 4,397,055 | 8/1983 | Cuchiara . | |
| 4,403,364 | 9/1983 | Schroeder | 15/38 |
| 4,740,706 | 4/1988 | Murdock, III | 312/209 |
| 4,796,323 | 1/1989 | Benz . | |
| 4,845,796 | 7/1989 | Mosley . | |
| 5,127,521 | 7/1992 | Bourque | 422/24 |
| 5,177,826 | 1/1993 | Vrignaud et al. . | |
| 5,177,827 | 1/1993 | Ellison . | |

FOREIGN PATENT DOCUMENTS

| | | | |
|---|---|---|---|
| 2916215 | 10/1980 | Germany | 15/23 |
| 3031940 | 4/1982 | Germany | 15/23 |
| 3347774 | 10/1984 | Germany | 15/23 |
| 3929461 | 3/1991 | Germany | 15/23 |
| 4019830 | 1/1992 | Germany | 15/23 |

Primary Examiner—Randall Chin
Attorney, Agent, or Firm—Terrance L. Siemens

[57] ABSTRACT

An electric rotary toothbrush having a flexible brush element which conforms to curvature of the teeth within the mouth. The flexible brush is supported at one end by attachment to the handle of the toothbrush, and at the other end by a wheel journaled to the shaft of the flexible brush. The wheel contacts and bears against the teeth or gums of the user. The wheel remains stationary while the brush rotates relative thereto. The toothbrush has a battery and reversible electric motor for rotating a shaft to which the brush is removably attached. The toothbrush is preferably provided with a cabinet for storing, sterilizing, and recharging the toothbrush.

9 Claims, 2 Drawing Sheets

FLEXIBLE ROTARY TOOTHBRUSH

BACKGROUND OF THE INVENTION

1. Field of the Invention

The present invention relates to a powered toothbrush having a rotatable, elongated, linear brush. The brush is flexible, and conforms to the overall configuration of the jaw. Brushing is accomplished with the brush inserted into the mouth and pressing against the teeth while rotating. A rotatable bearing disposed at the end of the brush leans against a surface of the teeth or gums, thereby providing a support for applying pressure causing the rotating brush to bear against the teeth and gums.

2. Description of the Prior Art

The task of cleaning by brushing, in general, and of cleaning teeth, in particular, has long been an onerous chore. There is a natural tendency to mitigate the effort required to clean thoroughly and effectively. To this end, brushes have been motorized, rotary motion being especially susceptible to automation by motorizing.

Care of teeth entails certain specific aspects and practices. For example, some authorities hold that brush strokes are more effective if applied in one direction than if constantly reciprocating. Rotary motion generally satisfies this requirement. Also, hygiene requires that all items of dental care be properly maintained clean and sterile.

U.S. Pat. No. 5,177,827, issued to Benedict M. Ellison on Jan. 12, 1993, describes a bifurcated brush having elongated brushing elements arranged to conform to curvature of the teeth as disposed upon the jaws. The elongated brushing elements rotate, and flex as they do so, but do not flex in the manner of the present invention. Flexing in the Ellison device results in rotation while maintaining the configuration of a "U". Flexing in the present invention causes the brush to conform to the mouth. Only one end of the brushing element in the present invention is connected to a source of rotary motion. In the device of Ellison, attachment is required at both ends. Ellison provides upper and lower brushing elements, therefore requiring a more complicated drive mechanism than that employed in the instant invention. Ellison also fails to teach the use of variable length bristles on a brushing element, as is practiced in the present invention. Ellison lacks a stationary support attached to a brush for contacting the surfaces of the mouth, which is a feature of the present invention.

An electric rotary brush which is reversible is shown in U.S. Pat. No. 3,451,086, issued to Elbert B. Burgett on Jun. 24, 1969. The brushing element is not flexible and lacks variable bristle length, both characteristics being found in the present invention. Burgett lacks the stationary support contacting surfaces of the mouth, as is found in the present invention.

A replaceable brushing head is featured in U.S. Pat. No. 3,822,432, issued to James A. Skinner on Jul. 9, 1974. Skinner also features a flexing drive shaft for rotating the brushing head. However, this drive shaft flexes to conform to a curved but rigid neck formed in the housing of the toothbrush. The brushing element itself does not flex, as contrasted with the present invention, and lacks a stationary support contacting surfaces of the mouth.

Compound motions of a brushing element are shown in U.S. Pat. Nos. 4,344,202, issued to Victor Hayat on Aug. 17, 1982, and 4,397,055, issued to Samuel M. Cuchiara on Aug. 9, 1983. The brushing elements of these two inventions rotate and reciprocate simultaneously, but do not flex in the manner of the present invention. There is no stationary support contacting surfaces of the mouth, as is found in the present invention.

None of the above inventions and patents, taken either singly or in combination, is seen to describe the instant invention as claimed.

SUMMARY OF THE INVENTION

The present invention provides an improved brush for cleaning irregular surfaces, such as human teeth. The brush effectively and automatically cleans the teeth and massages the gums. The brush has a flexible, linear, rotatable brush element which bends to conform to curvature established by the arrangement of teeth with respect to the jaw. The brush has bristles of different lengths, so that some bristles extend between adjacent teeth, while shorter bristles scrub the tooth surfaces. The brush element is manually removable for replacement.

The brush maintains a configuration corresponding to the dental arch or jaw configuration of the user by supports at either end of the brush. The brush is supported at one end by attachment to the handle. In a novel feature, the flexible brush is also supported at the other end, or distal end, by a bearing which rests against the teeth or gum. The bearing is stationary with respect to the teeth or gum, and is rotatably fixed to the flexible brush by a journaled connection.

Electrical circuitry incorporated within the brush includes a motor for rotating the brush, a battery for powering the motor, and a switch. The switch enables forward and reverse motor operation, so that the brush can be controlled to scrub in a direction from the gum to the teeth for either side of the mouth and for upper and lower teeth.

A storage cabinet is provided for storing, sterilizing, and recharging the brush. The storage cabinet is preferably mountable to a vertical environmental surface. A holder secures the brush in a predetermined position within the cabinet. In this position, electrodes of the brush contact cooperating electrodes provided in the cabinet. The electrodes of the brush are connected to the battery, so that correct positioning of the brush within the cabinet automatically results in recharging the battery.

The brush is sterilized when stored within the cabinet and the cover or door of the cabinet is closed. A door switch closes the electric circuit to a source of electromagnetic radiation of characteristics appropriate for destroying bacteria. Therefore, mere storage of the brush within its cabinet automatically results in sterilization. Preferably, the cabinet includes a plug and cord assembly for connection to household power.

Accordingly, it is one object of the invention to provide a powered, rotary brush having a flexible brush element for conforming to an irregular surface.

A second object of the invention is to support a flexible brush at two ends thereof.

A further object of the invention is to support the distal end of the brush by propping a stationary member against the teeth or gums, the brush rotating while journaled within the stationary member.

It is another object of the invention that the brush have a rechargeable battery power source.

It is a further object of the invention to enable operation of the motor in opposing directions.

Still another object of the invention is to enable manual replacement of the brush element.

An additional object of the invention is to provide automatic recharging of the battery.

It is again an object of the invention to provide automatic sterilization of the brush.

Yet another object of the invention is to provide bristles suitable for scrubbing an irregular surface.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
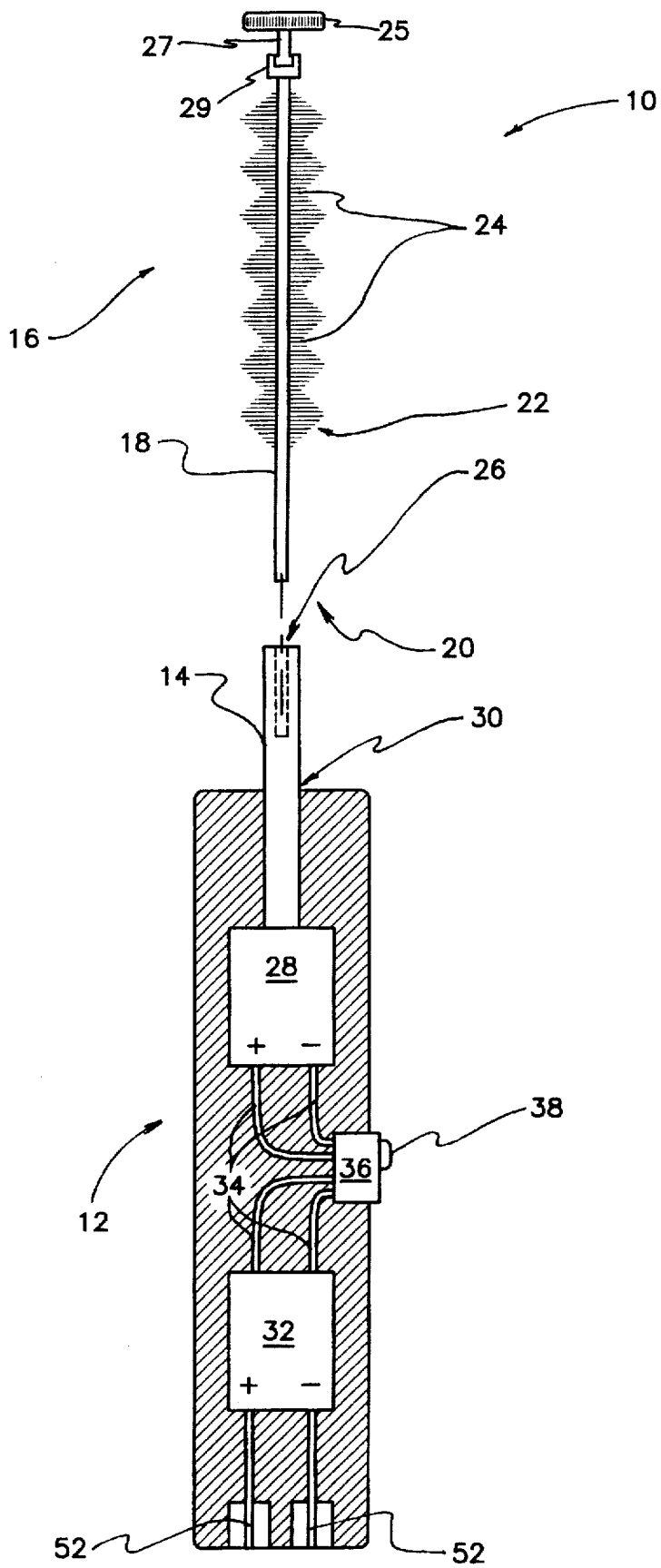
FIG. 1 is a side elevational, partially cross sectional view of the novel brush.

FIG. 1 shows the novel brush 10, which is seen to comprise a handle 12 serving as a housing enclosing electrical components, a drive shaft 14, and a brush 16. Brush 16 further comprises a shaft 18 which snap fits to or similarly manually engages drive shaft 14, and a brush element 20.

Brush element 20 preferably comprises bristles 22, which are seen to be of different or unequal length. Hereinafter, "different length" will be understood to refer to an arrangement defining periodically located depressions 24 in an otherwise cylindrical outer surface. As employed herein, "bristles" encompasses any resilient, liquid permeable material, such as foam rubber and foam plastic. Generally, the open arrangement of radiating bristles is superior for cleaning purposes. However, foams and other materials would be suitable for single usage applications.

Bristles 22 are disposed toward the distal end of shaft 18 (distal end should be understood to mean the end opposite to that which fits into the drive shaft 14). The proximal end of shaft 18 is devoid of bristles, in order to avoid interference while fitting closely in a socket 26 formed in drive shaft 14. Shaft 18 is flexible, so that it will conform to curvature of the teeth when pressed against the teeth and gums of the user (not shown). Shaft 18 grips socket 26 by friction, or in any other suitable way so that it is manually attachable and detachable at its proximal end to handle 12 through drive shaft 14. Brush element 20 may thus be removed and replaced for cleaning or other service when desired.

Depressions 24 accommodate an irregular surface (not shown), such as is encountered when brushing teeth. The irregular surface includes projecting surfaces of the teeth alternating with recesses, or gaps defined between adjacent teeth. Short bristles 22 contact projecting tooth surfaces (teeth are not shown) while longer bristles 22 extend into gaps existing between adjacent teeth, thereby assuring that when brush 10 is held in a constant position, all surfaces of the teeth are cleaned.

A bearing in the form of a wheel 25 is supported at the distal end of shaft 18 in a journaled arrangement. Axle 27 of wheel 25 is rotatably entrapped within the enlarged head 29 of shaft 18. When in use, wheel 25 contacts the teeth or gums (neither shown) of the user. Wheel 25 remains stationary, and enables the distal end of brush 16 to be propped against the mouth when rotating. This arrangement assists in maintaining brush 16 in a configuration cooperating with curvature of the teeth. Wheel 25 is attached to brush 10 solely by engagement with shaft 18 by entrapment of axle 27 within head 29 of shaft 18.

A motor 28 is connected to drive shaft 14, brush element 20 being rotated by drive shaft 14 when motor 28 operates. Drive shaft 14 is journaled at 30, or otherwise rotatably secured within handle 12.

Motor 28 is connected to a battery 32 by electrical conductors 34 through a switch 36 disposed in series with conductors 34. Switch 36 is preferably of the type making appropriate connection to motor 28 so as to operate motor 28 selectively in a forward direction and in a reverse direction. Motor 28 and battery 32 are preferably entirely contained within handle 12. Switch 36 projects to the outside, so that control knob 38 is accessible to the user.

Figure 2:
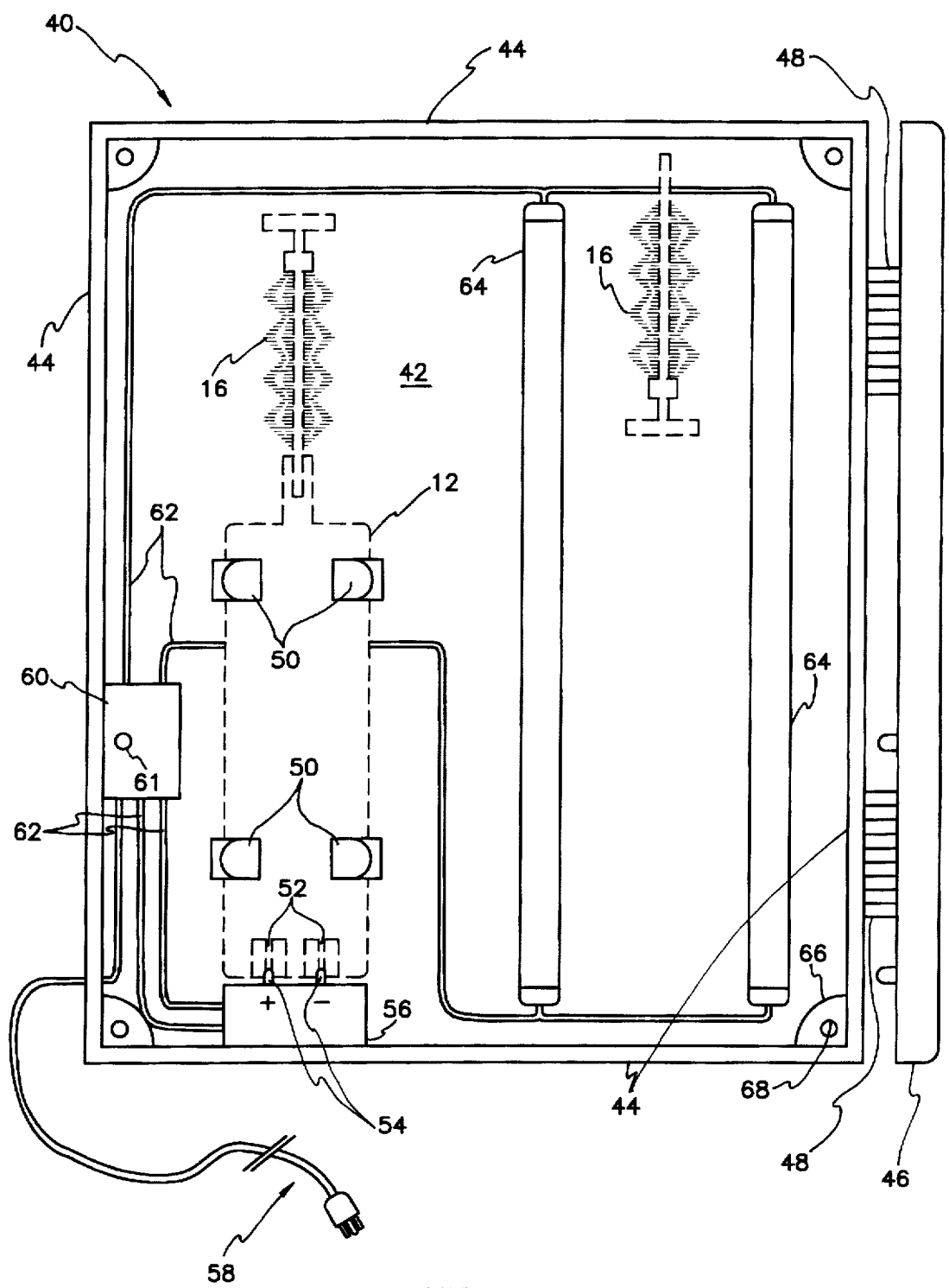
FIG. 2 is a front elevational, diagrammatic view of the storage cabinet.

Referring now to FIG. 2, a cabinet 40 is provided for storing, recharging, and sterilizing brush 10. Cabinet 40 has a rear wall 42, lateral walls 44, and a cover 46 attached to a lateral wall 44 by hinges 48. In the preferred embodiment of the invention, the cabinet 40 is made of a clear plastic material. Cover 46 is depicted open in a position ninety degrees to a closed position.

Clips 50 are provided to hold brush 10 in a stored position. In FIG. 2, brush 10 is shown in dashed lines to emphasize that brush 10 is removable from cabinet 40, and to readily discern components of cabinet 40 from those of brush 10.

It will be seen in FIG. 1 that brush electrodes 52 connect to battery 32, and are exposed at the bottom of handle 12. Again referring to FIG. 2, when brush 10 is held by clips 50, the bottom of handle 12 is pressed against cooperating cabinet electrodes 54 of a recharger 56. Recharger 56 includes a power converter (not separately shown) for converting household AC power to DC power for the purpose of charging battery 32.

Cabinet 40 has an electrical circuit for supplying recharger 56 and a sterilizer. The circuit includes a cord and plug assembly 58 for ready connection to household AC power, a switch 60, and conductors 62. Switch 60 closes the electrical circuitry supplying the sterilizer when cover 46 is in the closed condition, thereby automatically actuating the sterilizing feature. Switch 60 is preferably a limit switch having a projecting sensor 61 sensing proximity of cover 46 when cover 46 is closed.

The electrical circuit of cabinet 40 conducts power to a source of electromagnetic radiation, such as ultraviolet lamps 64 of characteristics appropriate for destroying bacteria. This arrangement sterilizes one or two brushes 16, which are removed from drive shall 14 and secured by clips (not shown) or in any other suitable way within cabinet 40 in effective proximity to lamps 64. In this preferred embodiment, the blue glow of the lamps would serve to remind people to brush their teeth and also would serve as a night light in the bathroom environment, Cabinet 40 preferably has bosses 66 drilled to include holes 68, for accepting fasteners (not shown), for wall mounting.

It will occur to those of skill in the art that modifications may be made to the embodiments set forth above, without departing from the spirit of the invention. For example, conductors 62 supplying recharger 56 may, if desired, be switched by switch 60. In another example, cabinet 40 may be large enough to contain spare brushes 16.

It is to be understood that the present invention is not limited to the embodiments described above, but encompasses any and all embodiments within the scope of the following claims.

I claim:

1. A rotary brush comprising:

a handle having a drive shaft and a motor for rotating said drive shaft carried within said handle;

a flexible shaft having a proximal end and a distal end, said flexible shaft having means for detachable securement to said drive shaft at said proximal end for rotation with said drive shaft;

a brush fixed on said flexible shaft near said distal end for rotation with said flexible shaft;

a bearing wheel journalled to said distal end of said flexible shaft, said bearing wheel attached solely to said flexible shaft, wherein, when said rotary brush is in use, said bearing wheel is placed in contact with the teeth and gums of a user forming a stationary rotational support for said distal end of said flexible shaft as said flexible shaft and said brush are rotated by said drive shaft and said motor.

2. The rotary brush according to claim 1, further comprising;

a battery carried within said handle for powering said motor;

electrical conductors electrically connecting said motor to said battery; and a switch disposed in series with said conductors, said switch having means for operating said motor selectively in a forward direction and in a reverse direction.

3. The rotary brush according to claim 1, wherein said brush has bristles of different length, whereby some of said bristles extend between adjacent teeth while brushing.

4. A rotary brush comprising:

a handle enclosing a drive shaft and a motor for rotating said drive shaft;

a battery carried within said handle for powering said motor;

electrical conductors electrically connecting said motor to said battery;

a switch means connected to said conductors for operating said motor selectively in a forward and reverse direction;

a flexible shaft detachably secured at a proximal end to said drive shaft for rotation with said drive shaft;

a brush including bristles of different lengths supported along said flexible shaft from near said proximal end to near a distal end for rotation with said flexible shaft;

a bearing wheel journalled to said distal end of, and supported solely by, said flexible shaft, wherein, when said rotary brush is in use, said bearing wheel is placed in contact with the teeth and gums of a user forming a stationary rotational support for said distal end of said flexible shaft as said flexible shaft and said brush are rotated by said drive shaft and said motor.

5. An electrically powered rotary brush and cabinet therefor, comprising:

a rotary brush having a handle;

a motor and drive shaft carried within said handle, said motor rotating said drive shaft;

a brushing means comprising a flexible shaft and a brush supported on said flexible shaft between proximal and distal ends thereof, said flexible shaft having means at said proximal end for manual detachable securement to and rotation with said drive shaft;

a battery carried within said handle for powering said motor;

electrical conductors electrically connecting said motor to said battery;

a switch disposed in series with said conductors, said switch having means for operating said motor selectively in a forward direction and in a reverse direction; and a cabinet having a rear wall, lateral walls, a hinged cover movable to a closed position, means for holding said rotary brush, a source of electromagnetic radiation for sterilizing said rotary brush, and an electrical circuit conducting electrical power to said source of electromagnetic radiation, said electrical circuit having a switch for closing said electrical circuit responsive to detection of said hinged cover being in the closed position, whereby said source of electromagnetic radiation sterilizes said rotary brush when said hinged cover is in the closed position.

6. The rotary brush and cabinet according to claim 5, said brushing means of said rotary brush further comprising a bearing wheel journalled to said distal end of and supported solely by said flexible shaft, wherein when said rotary brush is in use, said bearing wheel is placed in contact with the teeth and gums of a user forming a stationary rotational support for said distal end of said flexible shaft as said flexible shaft and said brush are rotated by said drive shaft and said motor.

7. The rotary brush and cabinet according to claim 5, said electrical circuit of said cabinet further comprising an electrical supply subcircuit having exposed electrodes, said rotary brush having cooperating second electrodes disposed to contact said electrodes of said electrical supply subcircuit and second conductors electrically connecting said battery to said second electrodes, whereby said battery of said rotary brush is automatically placed in contact with an electrical supply and thereby recharged when said rotary brush is held within said cabinet.

8. The rotary brush and cabinet according to claim 5, said brush having bristles of different length, whereby some of said bristles extend between adjacent teeth while brushing.

9. The rotary brush and cabinet according to claim 5, said cabinet further comprising means for mounting said cabinet to a vertical surface, and a plug and cord assembly electrically connected to said electrical circuit for connecting said electrical circuit to household electrical power.

* * * * *